United States Patent [19]
Van Peppen et al.

[11] 4,092,360
[45] May 30, 1978

[54] PRODUCTION OF CYCLOHEXANONE

[75] Inventors: Jan F. Van Peppen; William Bernard Fisher, both of Chester, Va.

[73] Assignee: Allied Chemical Corporation, Morris Township, N.J.

[21] Appl. No.: 793,563

[22] Filed: May 4, 1977

[51] Int. Cl.$^2$ .................. C07C 37/38; C07C 45/00
[52] U.S. Cl. ............................ 260/586 P; 568/754; 568/749
[58] Field of Search ............ 260/586 P, 621 A, 621 C

[56] References Cited
U.S. PATENT DOCUMENTS

| | | | |
|---|---|---|---|
| 3,187,050 | 6/1965 | Duggan et al. | 260/582 |
| 3,692,845 | 9/1972 | Cheema et al. | 260/621 A |
| 3,959,382 | 5/1976 | Yeh et al. | 260/586 P |
| 3,965,187 | 6/1976 | Little et al. | 260/586 P |

FOREIGN PATENT DOCUMENTS 892,562  2/1972  Canada .............................. 260/586 P

*Primary Examiner*—Norman Morgenstern
*Attorney, Agent, or Firm*—Fred L. Kelly

[57] ABSTRACT

In production of cyclohexanone by hydrogenating phenol in the presence of a hydrogenation catalyst, improved catalyst life and improved hydrogenation rate are obtained if ketone impurities, particularly hydroxyacetone, are removed from the phenol prior to the hydrogenation. The present invention provides an improved method for reducing the ketone impurities in the phenol by contacting the phenol with a polyethylenimine and distilling the mixture formed to separate the phenol. The invention is particularly useful in production of cyclohexanone from phenol obtained by decomposition of cumene hydroperoxide.

10 Claims, No Drawings

PRODUCTION OF CYCLOHEXANONE

CROSS-REFERENCES TO RELATED APPLICATIONS

This application is related to our copending application Ser. No. 744,538 filed Nov. 24, 1976.

BACKGROUND OF THE INVENTION

This invention relates to a process for preparing cyclohexanone. More particularly, this invention relates to a process for preparing cyclohexanone by hydrogenating phenol in the presence of a catalyst, using as starting material phenol obtained from fractional distillation of cumene hydroperoxide decomposition product.

The process whereby phenol is hydrogenated directly and selectively to cyclohexanone is well known. It is also well known that certain impurities present in commercial phenol effect the hydrogenation process. For example, the presence of iron, sulphur, and halogen, has been known to reduce catalyst efficiency and adversely effect selectivity.

In an effort to overcome these problems, the prior art has suggested the use of special catalysts and has further suggested certain pretreatment purification techniques prior to hydrogenation. None of these have met with too great of a success even though phenol having a purity of 99.9 percent is obtainable. In this respect it should be noted that impurities present in phenol when used in one commercial application such as the preparation of phenolic resins are not particularly significant in hydrogenation procedures. Accordingly, certain of the impurities which effect the colour stability of phenol do not effect the hydrogenability of phenol and vice-versa. Another reason for this lack of success is that commerical phenol is derived from a variety of sources and the impurities contained therein are of process environmental origin. Thus phenol obtained from the distillation of coal tar, or from the hydrolysis of chlorobenzene or from the dehydrogenation of cyclohexanol, will contain impurities which are different from those contained in phenol prepared by the cumene hydroperoxide process.

The production of phenol from cumene is well known. A typical process for obtaining phenol from cumene hydroperoxide, which has been obtained by liquidphase oxidation of cumene with molecular oxygen, involves forming a reaction mixture by continuously feeding the cumene oxidation product containing at least about 80 percent by weight of cumene hydroperoxide into a decomposer wherein the incoming hydroperoxide is diluted by cumene hydroperoxide decomposition products previously formed therein, maintaining the reaction mixture at elevated temperature, feeding to the reaction mixture a decomposition catalyst selected from the group consisting of sulfur dioxide and sulfuric acid, withdrawing reaction mixture from the decomposer, removing the decomposition catalyst from the product withdrawn form the decomposer, and fractionally distilling the resulting organic products to separately recover on acetone fraction, a phenol fraction and one or more by-products fractions. Patents relating to purification of phenol obtained by decomposition of cumene hydroperoxide include U.S. Pat. Nos. 2,597,497; 2,881,222; 2,910,511; 3,187,050; 3,692,845; 3,830,708; 3,896,006; and 3,965,187.

It is also known that the single most detrimental impurity contributing to the poisoning of catalyst systems when phenol is hydrogenated, is the presence of a specific carbonyl compound formed along with phenol during manufacture from the decomposition of cumene hydroperoxide. This specific carbonyl compound is known as 1-hydroxy-2-propanone, hydroxyacetone or acetol. More specifically, when phenol is hydrogenated in the presence of hydroxyacetone, the effectiveness of a hydrogenation catalyst is greatly reduced. This reduction of effectiveness is noted in two ways, firstly, in that the hydrogenation rate is decreased, and secondly, in that the catalyst life is greatly diminished. The most pertinent prior art is believed to be U.S. Pat. No. 3,965,187 which discloses that the catalytic hydrogenation of phenol obtained by the cumene hydroperoxide process is improved by hydrogenating high purity phenol containing not more than 75 ppm of hydroxyacetone. Hydroxyacetone-free phenol is obtained by treating phenol for 1–5 minutes with a polyamine such as hexamethylene diamine, hexamethylene triamine and the like or an aqueous solution thereof, and then distilling the mixture to separate the components.

The process for hydrogenation of phenol to cyclohexanone as disclosed in U.S. Pat. No. 3,965,187 is an important contribution to this art; however, the poisoning of metallic catalysts, e.g., palladium catalysts, has not been entirely eliminated in large scale commercial processes due to long-term accumulation of impurities, particularly nitrogen-containing impurities such as tricyclohexylamine, phenylcyclohexylamine and dicyclohexylphenylamine. We have now discovered that such impurities result from nitrogen-containing decomposition products formed from the polyamines introduced in accordance with the process of U.S. Pat. No. 3,965,187.

The present invention obviates these problems by providing an improved method for hydrogenating phenol wherein the effectiveness of the catalyst is greatly prolonged and hydrogenation rate increased.

SUMMARY OF THE INVENTION

The present invention may be summarized as follows: In a process for prparing cyclohexanone by hydrogenating phenol in the presence of a hydrogenation catalyst using as starting material phenol having a purity of at least 99.8 percent from distillation of cumene hydroperoxide decomposition product containing hydroxyacetone as an impurity, the improvement which comprises reducing the hydroxyacetone content of the phenol to a level less than 75 ppm by weight by heating the phenol for at least one minute at a temperature of 40° C. to 220° C. with 0.01 to 2 percent by weight of a polyethylenimine having a molecular weight of about 1,000 to 1,000,000, and distilling the mixture formed to separate the phenol.

Polyethylenimine is a highly branched polymer produced by the acid-catalyzed polymerization of ethylenimine in accordance with the equation:

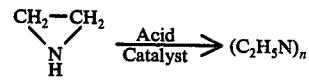

The polymer is composed of units which have two carbons per nitrogen, and these units are randomly distributed in the approximate ratios of one primary amino nitrogen/two secondary amino nitrogen/one tertiary amino nitrogen.

Polyethylenimine polymers have been known for many years but have had little commercial use until recently. At present, polyethylenimine polymers are valuable commercial products used most commonly as anchoring agents to bond similar or dissimilar materials together. Typical polyethylenimine polymers are available from the Dow Chemical Company.

The polyethylenimine interacts with or binds the hydroxyacetone present in such a manner that phenol free of the impurity can be recovered by distillation. This is a reversible reaction which involves the formation of water, and preferably the reaction mixture is swept with an inert gas to remove the water being formed, thereby eliminating the reversibility. The amount of polyethylenimine compound required is, to some extent, dependent upon the concentration of hydroxyacetone present in the phenol. In general, the amount of polyethylenimine used is 0.01–2.0 percent, preferably 0.03 to 1.0 percent, based on the weight of the phenol. The exact temperature at which the phenol is treated with the polyethylenimine compound is not critical. Generally, the treatment is carried out at 40°–220° C., preferably 60°–200° C. The period of treatment should be long enough to permit the desired reaction to take place. In general, substantial reaction can be obtained in one minute with a minimum time of 5 minutes being preferred.

The distillation whereby the phenol is freed from the ketonic impurities can be carried out at atmospheric pressure, reduced pressure or super-atmospheric pressure; preferably, distillation is carried out at atmospheric pressure or reduced pressure at 80°–182° C. depending upon the pressure in the system.

The prior art teaches many processes for hydrogenating phenol under varying reaction conditions and employing numerous catalysts systems and all of these are employable in the present invention. For example, the prior art indicates that phenol can be catalytically hydrogenated in liquid or vapor phase at 24°–400° C. and at pressures of 0 to 5,000 psig. Similarly, a variety of catalysts and catalyst supporting systems have been satisfactorily employed and any of the conventional hydrogenation catalysts are employable in the present invention. Exemplary of but few of these catalysts are nickel, platinum, cobalt, chromium oxide, palladium, and catalysts comprising mixtures of nickel, chromium, copper and molybdenum.

The aforementioned catalysts have been employed in amounts up to 10 percent, suspended in a liquid or supported on external surfaces (pellet or powder) of aluminum oxide, silica acid, diatomacious earth, charcoal, or Filter Cell and are present in only minor or catalytic amounts when considering the total catalyst charge in relationship to the total reaction mixture.

Although as previously stated the particular catalyst and reaction conditions are not critical, it must be appreciated that certain cataysts are less expensive and more active and selective for hydrogenating phenol directly to cyclohexanone, and it is expected that the choice of a particular catalyst will be governed accordingly. For our purposes, we prefer to use palladium, preferably palladium on carbon, with the palladium being in amounts of 0.2 to 10 percent by weight.

DESCRIPTION OF THE PREFERRED EMBODIMENT

The preferred process of the present invention may be stated as follows: In a process for preparing cyclohexanone by hydrogenating phenol in the presence of a palladium catalyst in the liquid phase at a temperature of 135° C. to 200° C., using as starting material phenol having a purity of at least 99.8 percent obtained from distillation of cumene hydroperoxide decomposition product containing hydroxyacetone as an impurity, the improvement which comprises reducing the hydroxyacetone content of the phenol to a level less than 30 ppm by weight by heating the phenol at a temperature of 60° C. to 200° C. for 5 to 100 minutes with 0.03 to 1 percent by weight of a polyethylenimine having a molecular weight of about 1,000 to 20,000, and distilling the mixture formed to separate the phenol.

In accordance with one preferred embodiment, the aforesaid purified phenol containing less than 30 ppm by weight of hydroxyacetone is hydrogenated to produce cyclohexanone by passing hydrogen in contact with the phenol in the presence of a palladium catalyst at 135° C. to 200° C., more preferably 145° C. to 185° C., said catalyst being further characterized in that it is composed of palladium coated carbon particles, said palladium being in amounts of 0.2–10 percent by weight based on the total weight of the catalyst, said carbon particles having diameters of 3 to 300 microns and a surface area of 100 to 2,000 m$^2$/gram, said phenol containing 10 to 300 ppm by weight of a promoter selected from the group consisting of alkali metal hydroxides, carbonates, phenates, bicarbonates and nitrates, the amount of said promoter being in terms of alkali metal of said promoter.

In order to illustrate the present invention, the following examples are given which exemplify the invention but should not be regarded as limiting the same. The parts and percentages employed are by weight unless otherwise indicated. The phenol used as starting material is obtained from distillation of cumene hydroperoxide decomposition product, has a purity of at least 99.8 percent but contains hydroxyacetone as an impurity.

EXAMPLE 1

The phenol starting material contains a total of 910 ppm of impurities of which 768 ppm are ketonic, including 576 ppm of hydroxyacetone. About 2500 parts of this phenol, and 7.5 parts of polyethylenimine having an average molecular weight of 1200 are heated at about 175° C. for about 60 minutes under a nitrogen sweep, then distilled at atmospheric pressure. Analyses of the distilled phenol show that it contains no hydroxyacetone and no nitrogen compounds. This demonstrates that the treatment with polyethylenimine removes the hydroxyacetone from the phenol and that the polyethylenimine does not decompose to give off volatile nitrogen compounds during the treatment. Similar results are obtained using polyethylenimines having a molecular weight between about 1,000 and 100,000; however, we prefer to use polyethylenimines having a molecular weight of about 1,000 to 20,000 because they are relatively less viscous.

EXAMPLE 2

This example illustrates the preferred process for hydrogenating phenol in the absence of hydroxyacetone to selectively produce cyclohexanone together with relatively small amounts of cyclohexanol. The phenol used is purified in accordance with Example 1 using polyethylenimine having an average molecular weight of 1,200.

The first of a series of five agitated hydrogenation vessels is charged with 45,694 parts per hour of said phenol, 1.3 to 2.0 parts of sodium carbonate, and 1,200 parts per hour of a sodium-promoted, palladium-on-carbon catalyst having a sodium content of 0.25–0.40 percent, said catalyst containing about 0.93 percent palladium on carbon particles having diameters of about 5 to 150 microns and a surface area of about 1000 m$^2$/gram. About 67 percent of the palladium on the catalyst is present as elemental palladium. Each hydrogenation vessel is connected in series so that the reaction mixture flows through the five vessels, the hydrogen being charged to the first vessel. The pressure is between 80 and 200 psig. The temperature in each vessel is as follows: 179° C. in the first vessel; 168° C. in the second vessel; 166° C. in the third vessel; 164° C. in the fourth vessel, and 162° C. in the fifth vessel. It is noteworthy for reasons of safety that the temperature in each vessel is less than 10° C. above the atmospheric boiling point of the reaction mixture present in the vessel. About 24,570 parts per hour of distillate, primarily cyclohexanone, is separated from the last three vessels; this distillate is rectified to provide substantially pure cyclohexanone. The reaction mass flowing from the fifth reaction vessel is fed to a continuous centrifuge, wherein the catalyst is separated from the crude cyclohexanone; the catalyst is recycled in the process. The crude cyclohexanone is rectified to recover substantially pure cyclohexanone which may be combined with the cyclohexanone recovered as described above.

In this continuous operation carried out for several months, cyclohexanone recovery is 42,856 parts per hour. Also recovered is 684 parts per hour of cyclohexanol, 1481 parts per hour of phenol, and 211 parts per hour of higher boiling by-products. Only 3 parts per hour of make-up catalyst is required in the process. Moreover, the recycled catalyst shows no build up of nitrogen-containing catalyst poisons such as tricyclohexylamine, phenylcyclohexylamine and dicyclohexylphenylamine.

EXAMPLE 3 (Comparative)

For comparative purposes, the procedure of Example 1 is followed except that hexamethylene triamine is used instead of polyethylenimine. With use of hexamethylene triamine, the hydroxyacetone is adequately removed from the phenol; however, the distilled phenol contained significant amounts of low molecular weight nitrogen compounds, including ammonia and amine compounds. In other tests the hexamethylene triamine lost 60 percent in weight when heated to 200° C. whereas the polyethylenimines are relatively stable at temperatures up to 200° C.

These results are consistent with our discovery that use of the process of U.S. Pat. 3,965,187 in large scale commercial processes leads to long-term accumulation of nitrogen-containing catalyst poisons including tricyclohexylamine, phenylcyclohexylamine and dicyclohexylphenylamine. The present invention obviates these problems.

We claim:

1. In a process for preparing cyclohexanone by hydrogenating phenol in the presence of a hydrogenation catalyst using as starting material phenol having a purity of at least 99.8 percent obtained from distillation of cumene hydroperoxide decomposition product containing hydroxyacetone as an impurity, the improvement which comprises reducing the hydroxyacetone content of the phenol to a level less than 75 ppm by weight by heating the phenol for at least one minute at a temperature of 40° C. to 220° C. with 0.01 to 2 percent by weight of a polyethylenimine having a molecular weight of about 1,000 to 100,000 and distilling the mixture formed to separate the phenol.

2. The process of claim 1 wherein the phenol is hydrogenated in the liquid phase in the presence of a hydrogenation catalyst comprising palladium.

3. The process of claim 1 wherein the phenol is heated with a polyethylenimine having a molecular weight of about 1,000 to 20,000.

4. The process of claim 1 wherein the phenol is heated with the polyethylenimine at a temperature of 60° C. to 200° C.

5. The process of claim 1 wherein the phenol is heated with 0.03 to 1 percent by weight of the polyethylenimine.

6. The process of claim 1 wherein the phenol is heated with the polyethylenimine for 5 to 100 minutes and the distilled phenol has a hydroxyacetone content less than 30 ppm.

7. The process of claim 1 wherein the phenol is heated with polyethylenimine at about 175° C. for about 60 minutes.

8. The process of claim 1 wherein the phenol is heated with the polyethylenimine while the mixture is swept with an inert gas.

9. In a process for preparing cyclohexanone by hydrogenating phenol in the presence of a palladium catalyst in the liquid phase at a temperature of 135° C. to 200° C. using as starting material phenol having a purity of at least 99.8 percent obtained from distillation of cumene hydroperoxide decomposition product containing hydroxyacetone as an impurity, the improvement which comprises reducing the hydroxyacetone content of the phenol to a level less than 30 ppm by weight by heating the phenol at a temperature of 60° C. to 200° C. for 5 to 100 minutes with 0.03 to 1 percent by weight of a polyethylenimine having a molecular weight of about 1,000 to 20,000, and distilling the mixture formed to separate the phenol.

10. The process of claim 9 wherein the palladium catalyst is further characterized in that it is composed of palladium coated carbon particles, said palladium being in amounts of 0.2–10 percent by weight based on the total weight of the catalyst, said carbon particles having diameters of 3 to 300 microns and a surface area of 100 to 2,000 m$^2$/gram, said phenol containing 10 to 300 ppm by weight of a promoter selected from the group consisting of alkali metal hydroxides, carbonates, phenates, bicarbonates and nitrates, the amount of said promoter being in terms of alkali metal of said promoter.

* * * * *